US010350373B2

(12) United States Patent
Patete et al.

(10) Patent No.: US 10,350,373 B2
(45) Date of Patent: Jul. 16, 2019

(54) INSTRUMENT FOR THE DEPOSITION OF ADIPOSE TISSUE IN LIPOMODELLING

(71) Applicant: POLITECNICO DI MILANO, Milan (IT)

(72) Inventors: Paolo Patete, Milan (IT); Guido Baroni, Milan (IT)

(*) Notice: Subject to any disclaimer, the term of this patent is extended or adjusted under 35 U.S.C. 154(b) by 820 days.

(21) Appl. No.: 14/420,104

(22) PCT Filed: Aug. 5, 2013

(86) PCT No.: PCT/EP2013/066418
§ 371 (c)(1),
(2) Date: Feb. 6, 2015

(87) PCT Pub. No.: WO2014/023701
PCT Pub. Date: Feb. 13, 2014

(65) Prior Publication Data
US 2015/0174341 A1    Jun. 25, 2015

(30) Foreign Application Priority Data

Aug. 9, 2012  (IT) .............................. MI2012A1424

(51) Int. Cl.
*A61M 5/48* (2006.01)
*A61M 5/315* (2006.01)
(Continued)

(52) U.S. Cl.
CPC .......... *A61M 5/484* (2013.01); *A61M 5/1452* (2013.01); *A61M 5/3158* (2013.01);
(Continued)

(58) Field of Classification Search
CPC .............. A61M 5/484; A61M 5/31576; A61M 5/14236; A61M 2005/31588;
(Continued)

(56) References Cited

U.S. PATENT DOCUMENTS 4,280,494 A * 7/1981 Cosgrove, Jr. ...... A61M 5/1723
604/503
5,322,511 A * 6/1994 Armbruster ............. A61M 5/20
604/152
(Continued)

FOREIGN PATENT DOCUMENTS

EP    1970094    9/2008
EP    2387962    11/2011

OTHER PUBLICATIONS

International Search Report for International Application No. PCT/EP2013/066418 issued by the European Patent Office dated Oct. 7, 2013.

*Primary Examiner* — Nathan R Price
*Assistant Examiner* — Justin L Zamory
(74) *Attorney, Agent, or Firm* — Stradley Ronon Stevens & Young, LLP

(57) ABSTRACT

A device for the deposition of adipose tissue, comprising: a) a syringe for grafting the tissue, b) a system for controlling the advance of the plunger of the syringe, which receives information about the movement of the syringe in the direction of withdrawal from an external system for detecting the movement of the syringe, and c) an external system for detecting the movement of the syringe. The control system determines the advance of the plunger of the syringe on the basis of the movement of the syringe in the direction of withdrawal and on the basis of the quantity of adipose tissue per unit of length of deposition. The advantages deriving from the use of this device in lipomodelling (or fat grafting) are in an automatic control of deposition of the adipose tissue and a correct uniformity of the graft.

19 Claims, 6 Drawing Sheets

(51) Int. Cl.
*A61M 5/145* (2006.01)
*A61M 5/31* (2006.01)

(52) U.S. Cl.
CPC . *A61M 5/31576* (2013.01); *A61M 2005/3125* (2013.01); *A61M 2005/31588* (2013.01); *A61M 2202/09* (2013.01); *F04C 2270/0421* (2013.01)

(58) Field of Classification Search
CPC ......... A61M 2005/14208; A61M 2005/14506; A61M 2202/09; G01B 7/003
See application file for complete search history.

(56) References Cited

U.S. PATENT DOCUMENTS

| | | | |
|---|---|---|---|
| 6,511,301 B1* | 1/2003 | Fugere | B05C 11/10 |
| | | | 222/251 |
| 6,524,250 B1 | 2/2003 | Weber et al. | |
| 7,632,251 B2 | 12/2009 | Lin et al. | |
| 2006/0229594 A1* | 10/2006 | Francischelli | A61N 7/02 |
| | | | 606/27 |
| 2008/0243057 A1* | 10/2008 | Jacobson | A61M 5/16886 |
| | | | 604/67 |
| 2009/0181104 A1* | 7/2009 | Rigotti | A61F 2/12 |
| | | | 424/574 |
| 2009/0275900 A1 | 11/2009 | Hetherington | |
| 2012/0209248 A1* | 8/2012 | Gurtner | A61M 5/1452 |
| | | | 604/506 |

\* cited by examiner

INSTRUMENT FOR THE DEPOSITION OF ADIPOSE TISSUE IN LIPOMODELLING

The present invention relates to the field of reconstructive plastic surgery, particularly to an instrument for the deposition of adipose tissue in what is known as lipomodelling or fat grafting (in the sense of lipomodelling with grafting of adipose tissue), and more particularly to an instrument which provides automatic control of the deposition of the adipose tissue and ensures the correct uniformity of grafting.

TECHNICAL BACKGROUND OF THE INVENTION

Autologous adipose tissue grafting is widely used in reconstructive plastic surgery for the correction of acquired or inherited morphological defects. In breast surgery, lipomodelling is used for the reconstruction of anatomical structures removed as a result of an operation, such as quadrantectomy or mastectomy, performed to remove a cancerous lesion. Recently, breast lipomodelling has also been used as an effective method of performing mastopexy or additive mastoplastic surgery, thus reducing post-operative problems caused by the use of prostheses.

Experimental evidence has shown that non-uniform distribution of the grafted adipose tissue may lead to post-operative complications, ranging from simple resorption of the grafted tissue (up to 60%) to necrotic tissue formation and the formation of adipose cysts. The onset of these complications is generally correlated with reduced angiogenesis in the grafted tissue, due to its concentration in limited areas of the breast.

Uniformity of distribution of the adipose tissue enables these complications to be reduced, by avoiding undesired accumulations.

At the present time, this problem is mainly overcome by the manual dexterity and sensitivity of the surgeon.

There are some lipomodelling instruments available that are intended to resolve the problem of achieving more accurate tissue grafting. For example, U.S. Pat. No. 7,632,251 and EP 2387962 describe a dispenser device comprising a pistol-like housing, a needle direction control mechanism, a boost mechanism, a quantity control mechanism, and a syringe positioning mechanism, wherein the syringe positioning mechanism is fixed on the pistol and coupled to the rear end of the needle direction control mechanism and has two syringe inlets with at least one syringe inlet joined to them. This device enables the syringe to be orientated with respect to the grip with an injected volume of between $\frac{1}{30}$ and $\frac{1}{240}$ cc per injection and allows the simultaneous injection of two components without their exposure to the air. This is achieved by means of a special mechanism of the trigger.

U.S. Pat. No. 6,524,250 describes a device for measuring and monitoring changes before, during and after a liposuction procedure, and for assisting in producing symmetrical body contours. The device comprises a remote control and data processing unit, a handheld ultrasound transducer, a monitor, and means for marking anatomical points to be measured. The ultrasound transducer is the essential element for guiding the surgeon in the course of the operation. This patent does not relate to the technical problem tackled by the present invention.

US20090275900 describes a syringe comprising a plunger activating system configured by means of gears to provide a one-way movement of the plunger as the body of the syringe is moved away from or towards the positioning guide.

U.S. Pat. No. 7,632,251 and EP2387962 have two fundamental drawbacks which prevent the described solution from resolving the technical problem of achieving uniform distribution of the grafted adipose tissue. The first and most important of these is the complete lack of control over the orientation and position of the instrument. Thus it is impossible to know where the adipose tissue is grafted, both in terms of direction and in terms of position within the channel created by the insertion of the syringe. The second drawback of the teachings of these patents is the "discretization" of the volume of tissue injected. This prevents the deposition of a continuous quantity of tissue in the direction of grafting, except by modulating this quantity during an individual deposition. Essentially, the prior art outlined above is simply a sophisticated version of an ordinary syringe.

US2009275900 provides control of the deposition of the tissue as a function of the rate of withdrawal of the syringe, but does not provide any feedback on the direction of grafting of the tissue. Furthermore, the proportionality of the volume of grafted tissue with respect to the withdrawal rate is not ensured in absolute terms, but only with respect to the supporting guide of the syringe which is held by the surgeon's hand: therefore, any movement of the hand prevents the accurate control of deposition. Moreover, the connection between the syringe and the guide is provided by fixed gears, which therefore do not allow the deposition of the adipose tissue to be modulated within a single direction of deposition.

Other systems are disclosed in US2012209248 and EP1970094.

As far as the inventors are aware, the devices illustrated in the documents cited above are not in use, and therefore not only do they fail to resolve the technical problem tackled by the invention, the solution of which is still dependent on the manual dexterity of the surgeon, but furthermore they have failed to gain acceptance in the clinical field.

The object of the present invention is to resolve the problems of the prior art, and specifically to ensure the uniform distribution of the adipose tissue during grafting, by means of the device described in the attached claims.

SUMMARY OF THE INVENTION

It has now been found that the aforesaid problems of the prior art, and particularly that of obtaining a uniform distribution of adipose tissue during grafting, are resolved by causing the means for controlling the advance of the plunger of the syringe used for adipose tissue grafting to communicate with an external system for detecting the position and movement of the syringe, and arranging for the degree of advance of the plunger, and therefore the quantity of adipose tissue deposited, to be determined by the processing of information on the position and movement of the syringe supplied by the external detection system.

One object of the present invention is a device for the deposition of adipose tissue, comprising:
a) a syringe (1) for grafting the tissue,
b) a system for controlling the advance of the plunger (5) of the syringe (1), which receives information about the movement of the syringe (1) in the direction of withdrawal from an external system for detecting the movement of the syringe, and
c) an external system for detecting the movement of the syringe, characterized in that the control system determines the advance of the plunger (5) of the syringe (1) on the basis of the movement of the syringe (1) in the direction of withdrawal and on the basis of the quantity of adipose tissue per unit length of deposition.

This device is useful for adipose tissue grafting, particularly autologous grafting, by the method known as lipomodelling.

By using the device of the present invention, a uniform distribution of the adipose tissue can be obtained, since the volume of tissue grafted per direction of insertion—the deposition pathways are created by the syringe at the time of its insertion—and within each of these directions is controlled, thus preventing undesired accumulations and non-uniformity of modelling.

The invention will now be described in detail, with the aid of drawings. The adipose tissue deposition system will also be referred to as SDTA.

DETAILED DESCRIPTION OF THE INVENTION

Figure 1:
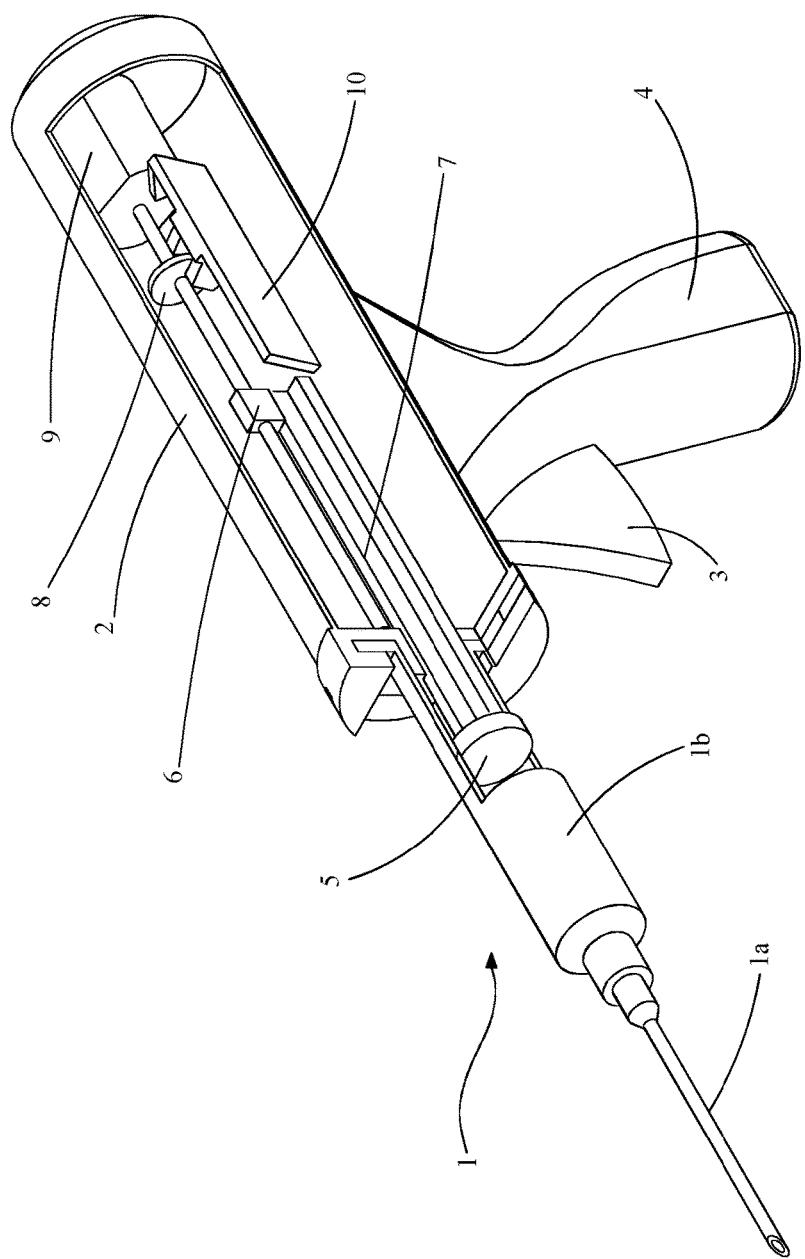
FIG. 1 shows an exploded perspective view of the system according to the present invention, in an exemplary embodiment.
Figure 2:
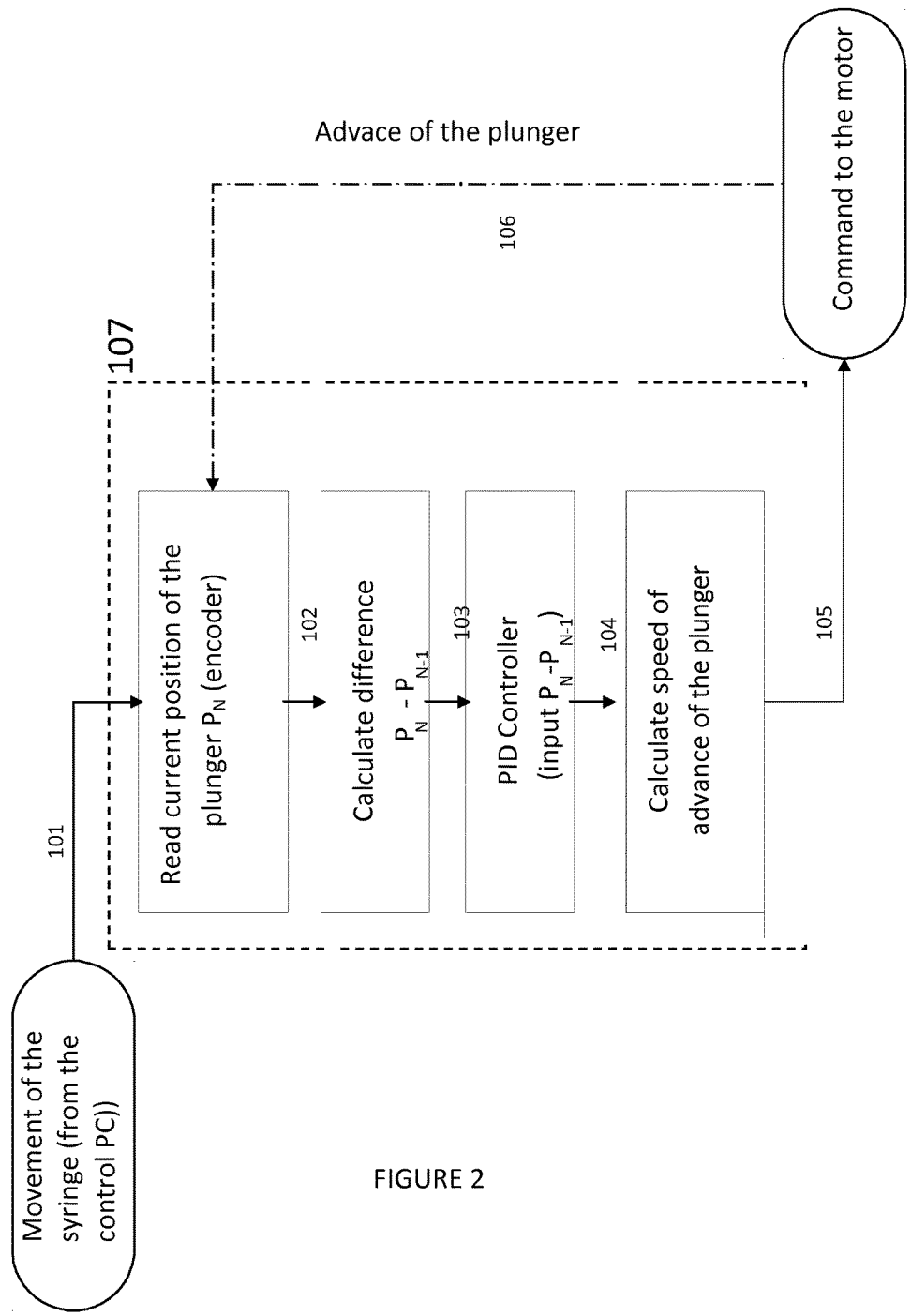
FIG. 2 shows a flow diagram of the data in the processor provided on the syringe.
Figure 3A:
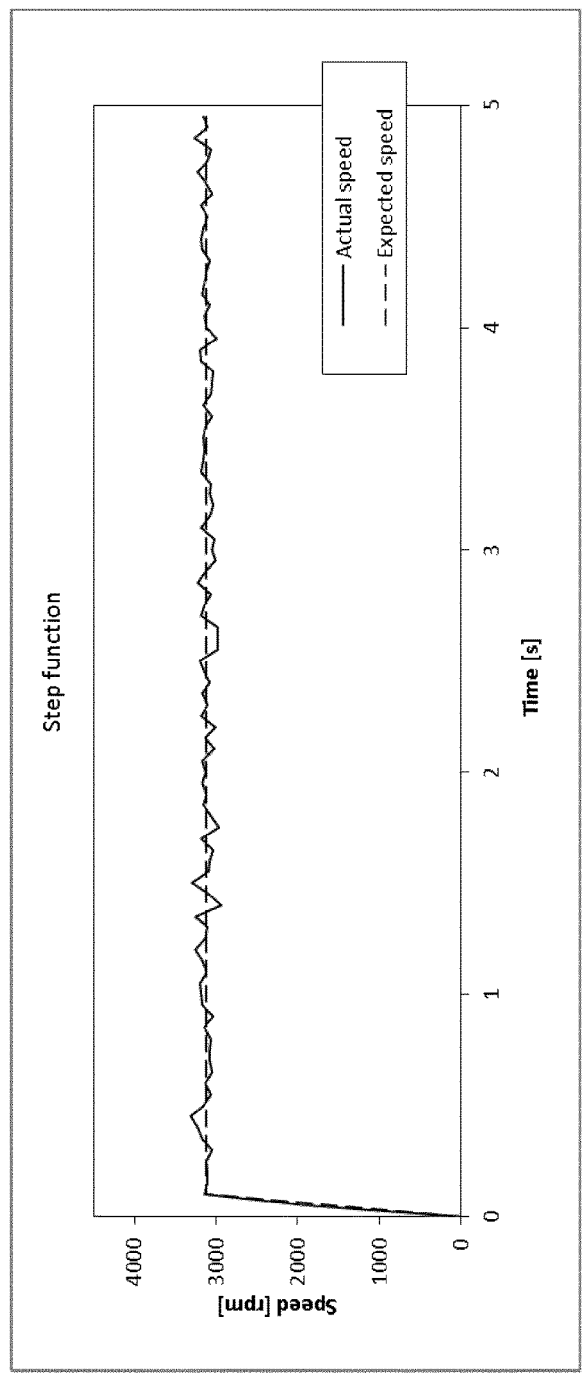
FIGS. 3A, 3B, 3C and 3D show the working performance of the system according to the present invention according to four modes: step function (A), increasing ramp (B), square wave (C) and decreasing ramp (D).
Figure 3B:
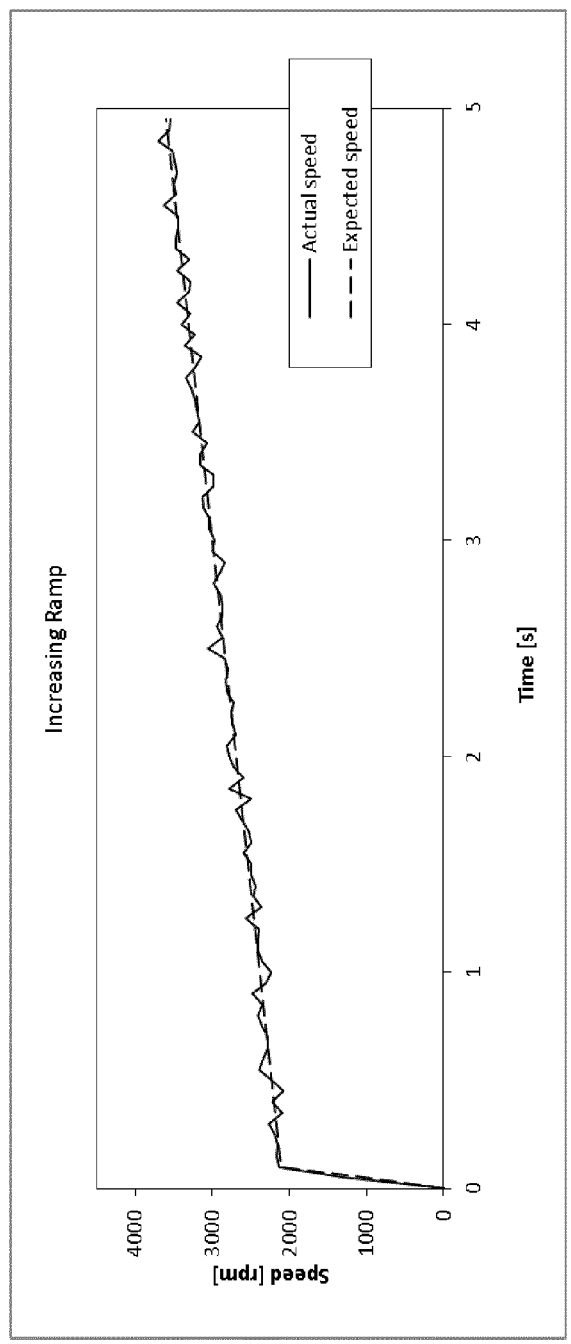
Figure 3C:
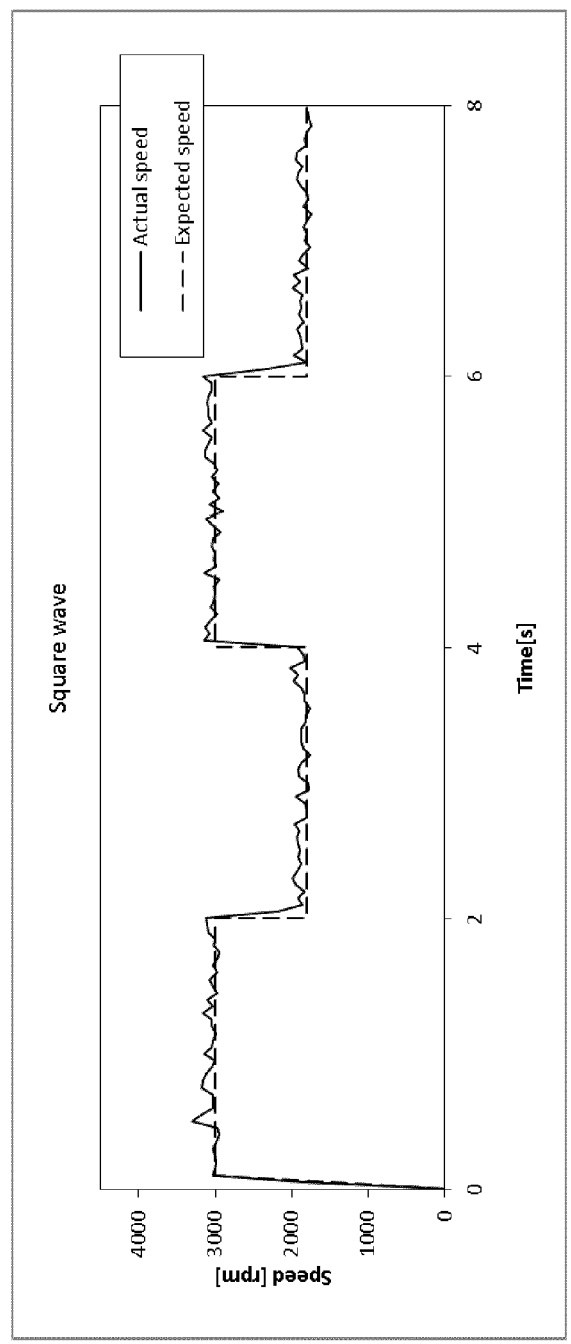
Figure 3D:
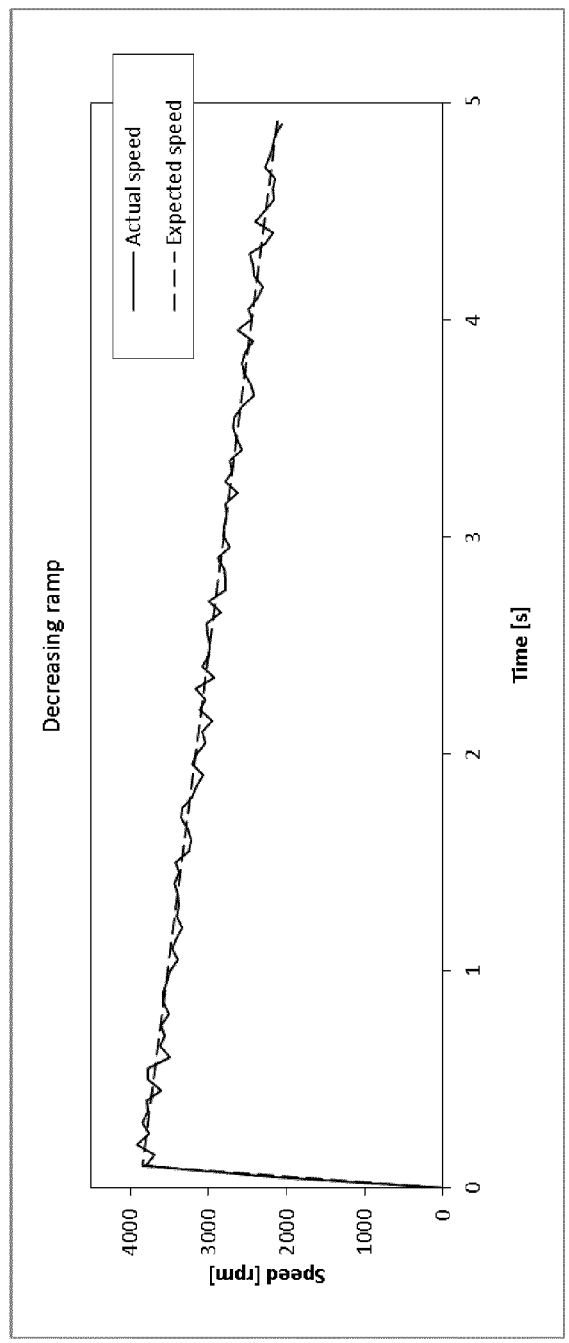

With reference to FIGS. 1 and 2 by way of example, the device according to the present invention comprises, in terms of its essential components, 1) a syringe (1) comprising a needle (1a), a syringe body (1b) and a plunger (5), the syringe being positioned on a suitable support, such that the syringe can be used for the operation of lipomodelling; this support is conveniently pistol-shaped (2);
2) means (9) for actuating the plunger (5), these means conveniently taking the form of an electric motor, preferably battery-powered;
3) means for specifying the volume of adipose tissue to be released (or to be grafted, in other words);
4) a position and movement detection system, preferably a tracking system, connected to the syringe (1), and
5) a control system (107), comprising a first processor adapted to receive in the form of an input (101) information from the system for detecting the position and movement of the syringe, and adapted to send in the form of an output a signal (105) to the means (9) for actuating the plunger (5), the processor comprising:
   a) means (102, 103, 104) for calculating the movement of the syringe in the direction of withdrawal and the degree of advance of the plunger;
   b) means (106) for comparing the calculated advance with the actual advance of the plunger (5); and
   c) an external system for detecting the position and movement of the syringe (1), connected to the control system defined in section 5) and comprising a second processor adapted to determine the position of the syringe (1) and to send information about the movement of the syringe (1) to the first processor.

The external detection system can be of any known type. In a preferred embodiment of the invention, the system is a tracking system.

Other possible detection systems include, for example, triangulation systems using radio frequency antennae.

The tracking system is of any known type, active or passive. The most preferred type of tracking system is optical, while a preferred type of system is electromagnetic. An ultrasound system can also be used. Combinations of suitably integrated systems, using what is known as the sensor fusion method (for example, an optical system coupled to inertial systems and miniaturized gyroscopic systems, or optical systems coupled to ultrasound systems), can be used to ensure maximum usability in the operating theatre, without imposing any restrictions on the surgeon's freedom of movement.

Conveniently, the second processor, which controls the external detection system and sends the information to the first processor of the system for controlling the plunger of the syringe, can be incorporated into a personal computer which may be portable.

In one embodiment of the present invention, the control system of the device can be provided with means for sending to the second processor, in the form of outputs, signals indicating the start and end of deposition and the amount of adipose tissue to be released. If the processor is incorporated into a computer, it can be connected to other systems of the computer in order to supply information to the surgeon carrying out the graft, examples of this information being a graphic or video representation of the deposition, or to supply a report on the progress of the graft.

FIG. 1 shows a view of the complete system (in exploded form) in an exemplary embodiment. The control peripherals and the detection system are omitted for the sake of clarity. Furthermore, the positions of the markers which form the detection system are not shown, since their arrangement can be entirely arbitrary. The motor support is fixed inside the pistol.

The integration of the components of the SDTA, namely the syringe (1), the tracking system and the control system, makes it possible to regulate the deposition of the autologous adipose tissue by moving the syringe (1). To this end, the device according to the present invention is provided with means for specifying the volume of tissue to be grafted per unit length of the deposition path ($cm^3$/mm). The means of specifying the volume may be mechanical, of a known type, or the volume may be specified by means of the control system forming part of the tracking system. By specifying a volume of tissue to be grafted and using software to calculate the movement of the syringe (1) in the direction of withdrawal, it is possible to determine the amount of adipose tissue to be released by an automatic advance of the plunger of the syringe (1). For the purposes of the present invention, the terms "withdrawal rate" and "movement of the syringe (1)" are used with equivalent meaning, since the rate is calculated as the instantaneous movement multiplied by the frequency of acquisition of the movement.

The communication between the SDTA control system and the tracking system, and therefore the integration between the two component parts of the invention, is provided by means of a connection, of the wireless type for example, such as a Bluetooth or other connection, through which data relating to the movement of the SDTA in space are sent to the microprocessor of the SDTA. These data are then used by the SDTA for the calculation of the advance of the plunger (5) of the syringe (1). In turn, and if desired, the SDTA sends to the aforesaid second control system, conveniently provided in a personal computer (PC), the information relating to the deposition of the adipose tissue (such as the instants of the start and end, the quantity injected, and the like), in such a way that this information can be displayed and a report on the operation can be produced. The information relating to the deposition of the adipose tissue is obtained by means of ordinary programming procedures. For example, the instants of the start and end of deposition are detected by the actuation and release of the pistol trigger, and the quantity injected is determined by a simple calculation algorithm. If the movement is controlled by means of an inertial unit, combined if necessary with other sensors of position, orientation and movement, the communication between the SDTA and the control computer takes place only for the purpose of sending the information relating to the grafting of the adipose tissue, since the information required for the calculation of the advance of the plunger of the syringe is directly available to the microprocessor because the latter is directly connected to the sensor or sensors that detect the movement of the SDTA in space.

Still with reference to FIG. 1, and to an exemplary embodiment of the present invention, the system is actuated by means of a "trigger" (3) which is inserted into a handle (4), to provide the greatest possible ease of manoeuvre for the surgeon. It is clearly evident that the shape of the trigger, or of any other means of actuating the system, particularly the piston, or plunger, and also the handle, are purely exemplary, and any other embodiment would fall within the scope of the present invention.

Conveniently, the handle of the "pistol" contains the control system, in other words all the control and communications electronics required for the operation of the SDTA. In particular, the first control system, comprising the first processor and the corresponding circuitry, is housed in the pistol-like support. In greater detail, the SDTA is composed of an electronic part and an electromechanical part, formed, respectively, by a set of peripherals required by the surgeon for interaction with the SDTA, and by means for advancing the plunger (5). These means can be of any known type, for example electromechanical or hydraulic. Conveniently, these means are formed by an electric motor (9), preferably powered by a battery.

With reference to FIG. 1, which shows an exemplary embodiment of the invention, the electromechanical part of the system is formed by a d.c. electric motor (9) which meets the requirements of compactness, lightness and efficiency. In a preferred embodiment of the invention, the motor has a working point of 7.5 V, a maximum current draw of 570 mA and a maximum speed of 6100 r.p.m. when unloaded. The characteristics of the motor can be varied without thereby departing from the scope of the present invention. The motor is connected to the piston (5) of the syringe (1) by means of a screw and nut system (6), with a threaded shaft typically having a diameter of 2.5 mm and a pitch of 0.5 mm. The nut is connected to a sliding block (7) to which the plunger is rigidly connected.

To control the operation of the motor correctly, the threaded shaft is connected to a rotary encoder (8) which ensures that the advance movement imparted to the nut on the shaft is matched by the actual advance of the plunger of the syringe. Finally, the motor is connected internally to the pistol by means of a support, which is shown by way of example by the number (10) in FIG. 1, although it is to be understood that the motor may be fixed in any convenient way.

The control electronics of the system are entirely contained within the pistol, for example in the grip of the support (4). The main functions controlled are the acquisition of the state of the peripherals (potentiometers, switches, etc.) and communication with the tracking system control system, a personal computer for example, which supplies in real time the desired advance of the plunger as a function of the movement of the syringe in the direction of withdrawal.

In one embodiment of the invention, the following additional peripherals are provided:
a) a potentiometer connected to the trigger of the pistol-like support to detect the pressure of the surgeon's finger;
b) a selector for specifying the operating mode, for example manual or automatic;
c) a push button for reversing the motion of the means for advancing the plunger (5), for example the electric motor (9);
d) a switch for switching the device on;
e) a pair of LEDs for displaying the states of the device, for example manual or automatic.

In one embodiment of the invention, the system for controlling the motor and the advance of the plunger is implemented by a PID (proportional integral derivative) controller. The input of the controller is represented by the desired advance, calculated on the basis of the speed detected by the SDTA, the flow rate of the syringe, and the data detected by the encoder. The motor is controlled by means of a closed-loop feedback system to increase or reduce its rotation speed in order to obtain the correct advance of the plunger.

The grafting of adipose tissue can take place in two modes, namely manual release, based on the pressure on the trigger, and automatic release, based on the detection of the speed of the SDTA.

In the first mode, the surgeon decides on the quantity of grafted tissue by pressing the trigger and obtains an advance of the plunger proportional to the pressure exerted. In the second case, however, the advance of the plunger is proportional to the movement of the syringe in the direction of withdrawal, and the movement is actuated by the same trigger (which acts solely as a switch in this case).

In a preferred embodiment of the invention, the automatic release of the plunger can be controlled in two distinct modes, depending on whether the detection of the speed takes place by means of an external tracking system, preferably optical, as explained above, or by the detection of the speed of withdrawal of the syringe using an inertial measurement unit with an inertial sensor. The type of system used to detect the movement of the syringe in the direction of withdrawal is not limiting for the purposes of the use of the invention. The device according to the present invention provides for the movement of the SDTA in the direction of withdrawal to be acquired automatically and accurately, providing a measurement on the basis of which the advance of the plunger is calculated.

The speed can be deduced from a measurement made with an accelerometer or with an inertial measurement unit, or from a calculation of the movement of the SDTA using a tracking system.

In the second case, markers (if an optical tracking system is used), or coils (if an electromagnetic tracking system is used), are positioned on the SDTA. The external tracking system supplies only the spatial coordinates of the markers (or of the system of coils) in the reference system of the tracking system. This information is then processed in order to locate the SDTA in space. The tracking system can therefore be of any type (optical, electromagnetic, ultrasound, etc.), provided that it supplies the required coordinates in real time so that the position and orientation of the SDTA in space can be identified unambiguously and consequently the movement of the syringe in the direction of withdrawal can be calculated. The positioning of the markers can be entirely arbitrary, since only three unaligned markers are used to identify the position of a rigid body in space, and the addition of further markers increases the accuracy of detection.

The use of inertial sensors to calculate the withdrawal speed of the SDTA is based on the acquisition of the linear acceleration of the instrument by means of an accelerometer, the output signal of which is integrated with respect to time to obtain the speed of the SDTA.

When the position of the SDTA in space and its movement in the direction of withdrawal of the syringe are known, the advance of the plunger can be controlled by means of the following equation:

$$\Delta S_{St} = \Delta S_{SDTA} \cdot \frac{V}{A}$$

in which $\Delta S_{St}$ is the movement of the plunger, $\Delta S_{SDTA}$ is the movement of the system along the axis of the syringe in the direction of withdrawal of the latter, $\hat{V}$ is the desired volume per unit length (cm³/mm) and A is the cross-sectional area of the syringe.

Finally, the controller, the operation of which may be based on a PID control system, ensures that the actual value of $\Delta S_{St}$ is equal to the calculated value, by comparing the predicted value of advance with that detected by the encoder.

With reference to FIG. 2, a mode of operation of the device of the present invention will now be illustrated.

The aforesaid second control system detects a movement (step 101) of the syringe (SDTA) and sends to the aforesaid first control system (107) a reading of the two positions defining the movement. These positions are detected by the detection system, which in the exemplary embodiment is a tracking system.

In the second control system (107), a first reading of the position of the plunger ($P_{N-1}$) is carried out. After the detection of the movement of the syringe, the second position of the plunger ($P_N$) is read. The two positions are read by means of the encoder (8 in FIG. 1). The first control system (107) calculates the difference between the two positions $P_N-P_{N-1}$ (step 102) and acts on the PID controller with the input $P_N-P_{N-1}$ (step 103).

On this basis, the speed of advance of the plunger is calculated (step 104). The first control system (107) then sends a command to the motor (9 in FIG. 1), which causes the plunger (5) of the syringe (1) to advance (step 106).

This cycle (102-106) is repeated indefinitely at the calculation frequency of the microprocessor (107) of the syringe (5), this frequency being much higher than the frequency of the tracking system.

Simulation tests have been carried out.

The desired speed is set to the motor (9) (dashed line in FIGS. 3A-3D) and the rotary encoder (8) connected to the motor (9) detects the real rotation speed. The difference between the real speed (solid line) and the desired one is sent to the PID controller, which calculates the new rotation speed of the motor (9) as to the detected speed is the closest to the desired value. Errors are mainly due to the encoder angular resolution and to the resolution of the square wave (PWM, Pulse Width Modulation) used to control the motor speed.

Uniformity of deposition is clearly shown.

The invention claimed is:

1. A device for the deposition of adipose tissue, comprising:

a) a syringe for grafting the tissue, the syringe having a plunger, a needle and a syringe body;
b) means for actuating the plunger;
c) means for specifying the volume of adipose tissue to be released per unit of length of deposition path;
d) an external system for detecting the movement of the syringe;
e) a position and movement detection system connected to the syringe; and
f) a system for controlling the advance of the plunger comprising a first processor adapted to receive in the form of an input information from the system for detecting the position and movement of the syringe, and adapted to send in the form of an output a signal to the means for actuating the plunger, the first processor comprising:
   i. means for calculating the movement of the syringe in the direction of withdrawal and the degree of advance of the plunger, according to the following equation $$\Delta S_{St} = \Delta S_{SDTA} \cdot \frac{V}{A}$$

in which $\Delta S_{st}$ is the movement of the plunger, $\Delta S_{SDTA}$ is the movement of the system along the axis of the syringe in the direction of withdrawal of the latter, V is the desired volume per unit length (cm³/mm) and A is the cross-sectional area of the syringe,
   ii. means for comparing the calculated advance with the actual advance of the plunger;
wherein the external system for detecting the movement of the syringe also detects the position of the syringe, the external detection system being connected to the control system and comprising a second processor adapted to determine the position of the syringe and to send information about the movement of the syringe to the first processor.

2. The device according to claim 1, wherein the external detection system is a tracking system.

3. The device according to claim 2, wherein the tracking system is selected from the group consisting of optical systems, electromagnetic systems, ultrasonic systems, and combinations of systems suitably integrated by what is known as the "sensor fusion" method.

4. The device according to claim 1, wherein the external detection system is a triangulation system using radio frequency antennae.

5. The device according to claim 1, wherein the external detection system is an inertial sensor.

6. The device according to claim 1, wherein the external detection system is a combination of one or more of (a) a tracking system; (b) optical systems, electromagnetic systems, ultrasonic systems, and combinations of systems suitably integrated by what is known as the "sensor fusion" method; c) triangulation system using radio frequency antennae; and (d) an inertial sensor.

7. The device according to claim 1, wherein the means for specifying the volume are mechanical.

8. The device according to claim 1, wherein the external detection system is a tracking system and the means for specifying the volume are provided by using the control system forming part of the tracking system to specify the volume.

9. The device according to claim 1, wherein communication between the system for controlling the advance of the plunger of the syringe and the external system for detecting the movement of the syringe is established by means of a connection.

10. The device according to claim 9, wherein the connection is of the wireless type.

11. The device according to claim 1, wherein the second processor is incorporated into a personal computer.

12. The device according to claim 1, wherein the control system is provided with means for sending to the second processor, in the form of outputs, signals indicating the start and end of the deposition and the amount of adipose tissue to be released.

13. The device according to claim 1, further comprising a pistol-like support and wherein the syringe is positioned on the pistol-like support.

14. The device according to claim 13, wherein the handle of the pistol-like support has a handle that contains the control system.

15. The device according to claim 1, wherein the system for controlling the advance of the plunger is electromechanical or hydraulic.

16. The device according to claim 15, wherein the system for controlling the advance of the plunger includes an electric motor.

17. The device according to claim 16, further comprising a rotary encoder and wherein the electric motor has a threaded shaft that is connected to the rotary encoder.

18. The device according to claim 14, wherein the pistol-like support has a trigger and the device further comprises:
a) a potentiometer connected to the trigger of the pistol-like support and adapted to detect the pressure of a surgeon's finger;
b) a selector for specifying the operating mode of the device;
c) a push button for reversing the motion of the system for controlling the advance of the plunger;
d) a switch for switching the device on; and
e) a pair of LEDs for displaying states of the device.

19. The device according to claim 16, further comprising a PID controller that controls the system for controlling the advance of the plunger.

* * * * *